United States Patent [19]
Dattagupta et al.

[11] Patent Number: 5,874,281
[45] Date of Patent: Feb. 23, 1999

[54] ENHANCEMENT OF OLIGONUCLEOTIDE INHIBITION OF PROTEIN PRODUCTION, CELL PROLIFERATION, AND/OR MULTIPLICATION OF INFECTIOUS DISEASE PATHOGENS

[75] Inventors: Nanibhushan Dattagupta, San Diego; C. Nagaraja Sridhar, Simi Valley; Daniel L. Kacian, San Diego, all of Calif.

[73] Assignee: Gen-Probe Incorporated, San Diego, Calif.

[21] Appl. No.: 967,385

[22] Filed: Oct. 8, 1997

Related U.S. Application Data

[63] Continuation of Ser. No. 366,937, Dec. 30, 1994, abandoned, and a continuation-in-part of Ser. No. 093,800, Jul. 19, 1993, abandoned.

[51] Int. Cl.⁶ .............................. C12N 7/06; C07H 21/04
[52] U.S. Cl. .......................... 435/238; 536/24.5; 935/34
[58] Field of Search .................. 514/44; 536/24.5; 435/238; 935/34

[56] References Cited

U.S. PATENT DOCUMENTS

| | | | |
|---|---|---|---|
| 4,689,320 | 8/1987 | Kaji | 514/44 |
| 4,806,463 | 2/1989 | Goodchild et al. | 435/5 |
| 4,851,330 | 7/1989 | Kohne | 435/6 |
| 5,023,243 | 6/1991 | Tullis | 514/44 |
| 5,030,557 | 7/1991 | Hogan et al. | 435/6 |
| 5,110,802 | 5/1992 | Cantlin et al. | 514/44 |
| 5,166,195 | 11/1992 | Ecker | 514/44 |
| 5,190,931 | 3/1993 | Inoyue | 435/91 |
| 5,208,149 | 5/1993 | Inoyue | 435/91 |
| 5,252,723 | 10/1993 | Bhatt | 536/25.3 |
| 5,264,423 | 11/1993 | Cohen et al. | 514/44 |
| 5,739,309 | 4/1998 | Dattagupta et al. | 536/24.5 |

FOREIGN PATENT DOCUMENTS

| | | |
|---|---|---|
| 0288163 | 3/1988 | European Pat. Off. |
| 0309230 | 3/1989 | European Pat. Off. |
| 9315194 | 8/1983 | WIPO |
| 8902896 | 4/1989 | WIPO |
| 9115580 | 10/1991 | WIPO |
| 9118004 | 11/1991 | WIPO |
| 9207864 | 5/1992 | WIPO |
| 9214843 | 9/1992 | WIPO |

OTHER PUBLICATIONS

TM Woolf et al (1992) Proc Natl Acad Sci USA 89:7305–7309.

DJ DeNoon (1995) IAC Newsletter DB Accession No. 02944476.

Bock et al., "Selection of single–stranded DNA molecules that bind and inhibit human thrombin," *Nature* 355:564–566 (1992).

Britten and Davidson, "Hybridization Strategy." in *Nucleic acid hybridization – a practical approach*, ed. B.D. Hames and S.J. Higgins, (Washington D.C.: IRL Press, 1985) 3–15.

Burke and Berzal–Herranz, "In vitro selection and evolution of drug discovery," *FASEB* 7:106–112 (1993).

Cullen, "Trans–Activation of Human Immunodeficiency Virus Occurs via a Bimodal Mechanism," *Cell* 46:973–982 (1980).

Ellington and Szostak, "In vitro selection of RNA molecules that bind specific ligands," *Nature* 346:818–822 (1990).

(List continued on next page.)

*Primary Examiner*—Bruce R. Campell
*Attorney, Agent, or Firm*—Lyon & Lyon LLP

[57] ABSTRACT

The invention features the use of a purified first targeted oligonucleotide in combination with either 1) a subtargeted oligonucleotide, 2) second targeted oligonucleotide, or 3) a non-targeted phosphorothioate oligonucleotide, to inhibit protein production of a targeted nucleic acid sequence, cell proliferation, and/or the multiplication of a foreign organism. The subtargeted oligonucleotide contains a truncated version of the targeted oligonucleotide.

15 Claims, 1 Drawing Sheet

OTHER PUBLICATIONS

Goodchild, "Ribozyme Kinetics and Optimization," *Third International Symposium on Catalytic RNAs (Ribozymes) and Targeted Gene Therapy for the Treatment of HIV Infection*, Dec. 6–11, 1992, San Diego, California.

Goodchild et al., "Inhibition of human immunodeficiency virus replication by antisense oligodeoxynucleotides," *Proc. Natl. Acad. Sci. USA* 85:5507–5511 (1988).

Green et al., "In vitro genetic analysis of the Tetrahymena self-splicing intron," *Nature* 347:406–408 (1990).

Helene and Toulme, "Specific regulation of gene expression by antisense, sence and antigene nucleic acids," *Chemica et Biophyscia Acta* 1049:99–125 (1990).

Liebhaber et al., "Inhibition of mRNA Translation by Antisense Sequences," *Gene Regulation: Biology of Antisense RNA and DNA*, eds. R.P. Erickson and J.G. Izant, (New York: Raven Press, Ltd., 1992) 163–174.

Maher et al., "Specific Hybridization Arrest of Dihydrofolate Reductase mRNA in Vitro using Anti-sense RNA or Anti-sense Oloigonucleotides," *Arch Biochem Biophys* 253:214–220 (1987).

Majumdar et al., "Stepwise Mechanism of HIV Reverse Transcriptase: Primer Function of Phosphorothioate Oligodeoxynucleotide," *Biochemistry* 28:1340–1346 (1989).

Matsukara et al., "Regulation of viral expression of human immunodeficiency virus in vitro by an antisense phosphorothioate oligodeoxynucleotide agaisnt rev (art/trs) in chronically infected cells," *Proc. Natl. Acad. Sci. USA* 86:4244–4248 (1989).

McGilvery and Goldstein, "Biochemistry: A Functional Approach," (Philadelphia, W.B. Saunders Company, 1983) pp. 61–63.

Nelson et al., "Detection Of Acridinium Esters By Chemiluminescence" in: *Nonisotopic DNA Probe Techniques*, Kricka ed., Academic Press, pp. 275–311 (1992).

Ratner et al., "Complete Nucleotide Sequence of the AIDS Virus, HTLV–III," *Nature* 313:277–284 (1985).

Robertson and Joyce, "Selection in vitro of an RNA enzyme that specifically cleaves single-stranded DNA," *Nature* 344:467–468 (1990).

Rossi et al., "Ribozymes as Anti–HIV–1 Therapeutic Agents: Principles, Applications, and Problems," *Aids Research and Human Retroviruses* 8:183–189 (1992).

Schwartz et al., "Cloning and Functional Analysis of Multiply Spliced mRNA Species of Human Immunodeficiency Virus Type I," *Journal of Virology*, 64:2519–2529 (1990).

Tenover, "Diagnostic Deoxyribonucleic Acid Probes for Infectious Diseases," *Clinical Microbiology Reviews* 1:82–101 (1988).

Uhlmann and Peyman, "Antisense Oligonucleotides: A New Therapeutic Principle," *Chemical Reviews* 90:544–584 (1990).

Zuker, "Computer Prediction of RNA Structure," *Methods in Enzymology* 180:262 (1989).

CF Bennett et al (1996) Science 271:434.

JF Milligan et al (1993) J Med Chem 36: 1923–1937.

P Westermann et al (1989) Biomed Biochim Acta 48:85–93.

N Miller et al (1994) Parasitology Today 10: 92–97.

RA Stull et al (1995) Pharmaceutical Research 12: 465–483.

S Wu–Pong (1994) Pharmaceutical Technology 118: 102–114.

RW Wagner (1994) Nature 372: 333–335.

JS Cohen (1992) Trends in Biotechnology 10: 87–91.

B Dropulic et al (1994) Human Gene Therapy 5: 927–939.

PA Pizzo et al (1994) Clinical Infectious Diseases 19: 177–196.

ER Kern (1990) In: Antiviral Agents and Viral Diseases of Man, 3rd edition, GJ Galasso et al, eds, pp. 94–95.

Sacramento Bee (Feb. 26, 1994) p. A22.

Sacramento Bee (Nov. 29, 1991) p. B5.

H Collins (Mar. 6, 1993) Philadelphia Inquirer p. A01.

Gartner and Popovic, Virus Isolation and Production, pp. 53–70 in *Techniques in HIV Research*, ed. by A. Alaldocini and B.D. Walker. Stockton Press. N.Y. (1990).

Goodchild, "Enhancement of ribozyme catalytic activity by a contiguous oligodeoxynucleotide (facilitator) and by 2'–O–methylation," *Nucleic Acids Research* 20:4607–4612 (1992).

Kinchington et al., "A comparison of gag, pol and rev antisense oligodeoxynucleotides as inhibitors of HIV–1," *Antiviral Research* 17:53–62 (1992).

Maher and Doinick, "Comparative hybrid arrest by tandem antisense oligodeoxyribonucleotides or oligodeoxy–ribonucleotides methylphosphonates in a cell–free system," *Nucleic Acids Research* 16:3341–3358 (1988).

Mills et al., "An Extracellular Darwinian Experiment with a Self–Duplicating Nucleic Acid Molecule," *Proc. Natl. Acad. Sci. USA* 58:217–224 (1967).

Strobel and Dervan, "Cooperative Site Specific Binding of Oligionucleotides to Duplex DNA," *J. Am. Chem. Soc* 111:7286–7287 (1989).

Tuerk and Gold, "Systematic Evolution of Ligands by Exponential Enrichment: RNA Ligands to Bacteriophage T4 DNA Polymerase," *Science* 249:505–510 (1990).

Weislow et al., "New Soluble–Formazan Assay for HIV–1 Cytopathic Effects: Application to High–Flux Screening of Synthetic and Natural Products for AIDS–Antiviral Activity," *J. Natl. Cancer. Inst.* 81:577–586 (1989).

Denman et al., "Cleavage of full length βAPP mRNA hammerhead ribozymes," *Nucleic Acids Research* 21:4119–4125 (1993).

Fig. 1

| TARGET SITE - 1 | 5'—— CCCGAGGGGACCCGACAGGCCCGAAG —— 3' |

SUBTARGETED OLIGONUCLEOTIDE  3'    CCCTGGGCTGTCCG    5'
(SEQ. ID. NO. 3)

TARGETED OLIGONUCLEOTIDE  3'   GGGCTCCCCTGGGCTGTCCGGGCTTC  5'
(SEQ. ID. NO. 1)

Fig. 2

ENHANCEMENT OF OLIGONUCLEOTIDE INHIBITION OF PROTEIN PRODUCTION, CELL PROLIFERATION, AND/OR MULTIPLICATION OF INFECTIOUS DISEASE PATHOGENS

RELATED APPLICATION

This application is a continuation of application Ser. No. 08/366,937 filed 30, Dec. 1994 abandoned, which is a continuation-in-part of Dattagupta et al., U.S. application Ser. No. 08/093,800 entitled "Enhancement of Oligonucleotides Inhibition of Protein Production, Cell Proliferation, and/or Multiplication of Infectious Disease Pathogens" filed Jul. 19, 1993, abandoned.

BACKGROUND OF THE INVENTION

This invention relates to enhancing the ability of oligonucleotides, such as antisense oligonucleotides and ribozymes, to inhibit protein production, cell proliferation, and/or the multiplication of a foreign organism.

Oligonucleotides such as antisense oligonucleotides and ribozymes can hybridize to a target RNA, such as mRNA, and inhibit production of protein from that RNA. Numerous mechanisms have been proposed to explain the effects of antisense oligonucleotides. For example, see Helene, C. and Toulme, J. *Biochimica et Biophysica Acta* 1049:99 (1990), and Uhlmann, E. and Peyman, A. *Chemical Reviews* 90:543 (1990). Proposed mechanisms include formation of a DNA:RNA substrate for cellular RNAse H, which degrades the RNA strand involved in the duplex; hybridization of an antisense oligonucleotide to nascent mRNA leading to premature transcription termination; and interfering with mRNA processing by hybridizing to a pre-mRNA intron/exon junction. These and several other proposed mechanisms for inhibiting nucleic acid activity by antisense oligonucleotides are based upon the ability of antisense oligonucleotides to hybridize to a target RNA sequence.

Oligonucleotides can also inhibit viruses by a sequence non-specific mechanism. For example, Majumdar, et al., *Biochemistry* 28:1340 (1989) describe the use of phosphorothioate oligonucleotides to inhibit HIV reverse transcriptase.

Hybridization of an oligonucleotide to a target nucleic acid sequence occurs by hydrogen bonding between complementary nucleotides present on the oligonucleotide and the nucleic acid target site. If the individual nucleotides on the target nucleic acid sequence are not accessible to the oligonucleotide, hybridization will be prevented. Inaccessibility of nucleotides can be due to various factors such as secondary structure of the target nucleic acid and proteins associated with target nucleic acid.

Hogan, et al., U.S. Pat. No. 5,030,557, describe the use of a "helper" oligonucleotide to help a probe oligonucleotide hybridize to its target nucleic acid sequence in a diagnostic assay.

Goodchild, J., Abstract in *Third International Symposium On Catalytic RNAs (Ribozymes) And Targeted Gene Therapy For The Treatment Of HIV Infection,* San Diego Calif. (1992), describes the use of "facilitators" to improve the performance of hammerhead ribozymes. Facilitators are oligoribonucleotides that bind to a RNA substrate target sequence contiguously with a ribozyme binding site.

Tullis, U.S. Pat. No. 5,023,243, provides a general description of use of antisense oligonucleotides. Kaji, U.S. Pat. No. 4,689,320, provides data allegedly showing a decrease in mortality in mice infected with herpes simplex virus when treated with an antisense oligonucleotide having a nucleotide sequence targeted to herpes simplex virus. Goodchild et al., U.S. Pat. No. 4,806,463, provide data to demonstrate the ability of several different specified antisense oligonucleotides to inhibit HTLV-III (HIV) replication and gene expression in cultured cells infected with HIV. Cantin et al., U.S. Pat. No. 5,110,802, describe the use of a particular methylphosphonate-linked oligonucleotide to inhibit HIV replication (these U.S. patents are hereby incorporated by reference herein).

Matsukura et al., *Proc. Natl. Acad. Sci.* 86:4244, describe inhibition of HIV expression without killing the host cell using a phosphorothioate-linked oligonucleotide targeted to a rev sequence. Matsukura et al. also discuss using oligonucleotides joined by linkages other than phosphodiester or phosphorothioate groups. According to Matsukura et al., "certain chemically modified oligomers (e.g., methylphosphonates) have inherent limitations in that they are quite insoluble and require exceedingly high concentrations for biological effects."

Ribozymes, like antisense oligonucleotides, can be targeted to specific nucleic acid sequences based upon hybridization to a complementary nucleic acid sequence target site. The hybridized ribozyme can inhibit protein production from a target nucleic acid sequence by cleaving the nucleic acid sequence. Rossi et al., *Aids Research And Human Retroviruses* 8:183 (1992), in discussing using ribozymes as possible anti-HIV therapeutic agents, mention potential factors which may decrease accessibility of a target site. These factors may include HIV RNA having extensive secondary structure and cellular proteins associated with RNA.

Ribozymes and antisense oligonucleotides can be used to inhibit the functioning of nucleic acid sequences present in different organisms such as bacteria, plants, fungi, animals, or humans. For example, Fung et al., entitled "Gene therapy for cell proliferative diseases," PCT/US91/02478, discuss using ribozymes in humans to inhibit the functional expression of positive-acting growth regulatory elements to treat pathological cell proliferative diseases. Fung et al. also mention using antisense RNA as a means of suppressing gene expression.

SUMMARY OF THE INVENTION

The present invention features methods and compositions for enhancing the ability of an oligonucleotide to inhibit protein production, cell proliferation and/or the multiplication of a foreign organism. The featured oligonucleotide compositions have a first targeted oligonucleotide and either, 1) a subtargeted oligonucleotide, 2) a second separately targeted oligonucleotide, or 3) a non-targeted phosphorothioate oligonucleotide.

The first targeted oligonucleotide is designed to hybridize to a target nucleic acid sequence. Hybridization between an oligonucleotide and a nucleic acid sequence occurs by complementary hydrogen bonding. While targeted oligonucleotides are designed to hybridize to a nucleic acid sequence, the effect of a targeted oligonucleotide on protein synthesis and/or viral multiplication is not limited to effects caused by hydrogen bonding to a complementary nucleic acid sequence. For example, targeted oligonucleotides may inhibit protein catalytic ability.

The subtargeted oligonucleotide is designed to hybridize to a subtarget region of the target region of the first targeted oligonucleotide. Thus, a subtargeted oligonucleotide contains a truncated portion of a first targeted oligonucleotide.

The ability of a subtargeted oligonucleotide, like a targeted oligonucleotide, to inhibit protein synthesis and/or viral multiplication is not limited to a mechanism involving hydrogen bonding between nucleotides.

The second targeted oligonucleotide is designed to hybridize to a different region than the first targeted oligonucleotide. Preferably, the target region of the second targeted oligonucleotide is located more than three nucleotides away from the target region of the first targeted oligonucleotide.

Targeted oligonucleotides, such as antisense oligonucleotides and ribozymes, can be designed to hybridize to cellular and viral nucleic acid sequences based upon complementary hydrogen bonding between nucleotides. The hybridized oligonucleotide then inhibits the nucleic acid activity of the target nucleic acid.

"Non-targeted phosphorothioate oligonucleotide" refers to an oligonucleotide joined by phosphorothioate linkages, which can function in a non-sequence specific manner. For example, see Majumdar, et al., supra, hereby incorporated by reference herein.

The described oligonucleotide compositions are particularly useful for inhibiting the nucleic acid activity of a target nucleic acid. The activity of target nucleic acid is that activity needed for protein production or nucleic acid replication. Target nucleic acid includes nucleic acid present in different types of organisms such bacteria, plants, fungi, parasites, viruses, and animals. Generally, the activity of target nucleic acid includes transcription of RNA, translation of mRNA, processing of mRNA, stability of mRNA, and replication of both RNA and DNA.

The activity of viral nucleic acid is that activity needed for viral multiplication. For example, HIV nucleic acid activity needed for replication includes reverse transcription of HIV RNA, translation of HIV mRNA, processing of HIV mRNA, packaging of genomic HIV RNA, and HIV RNA stability. The importance of a particular type of nucleic acid activity can vary in different types of viruses.

Thus, in a first aspect, the invention features a method and compositions for reducing the level of, or inhibiting, protein production coded for by a target nucleic acid. The method involves using a purified targeted oligonucleotide and a purified subtargeted oligonucleotide. These oligonucleotides are targeted to a nucleic acid sequence present on the target nucleic acid. Target nucleic acid sequences include mRNA coding for a protein or corresponding genomic and/or regulatory sequences. The subtargeted oligonucleotide comprises a truncated version of the targeted oligonucleotide.

By "purified" is meant to exclude naturally occurring oligonucleotides. Purified oligonucleotides may be produced by techniques known in the art such as chemical synthesis and by in vitro or in vivo expression from recombinant nucleic acid molecules, e.g., retroviral vectors.

Figure 1:
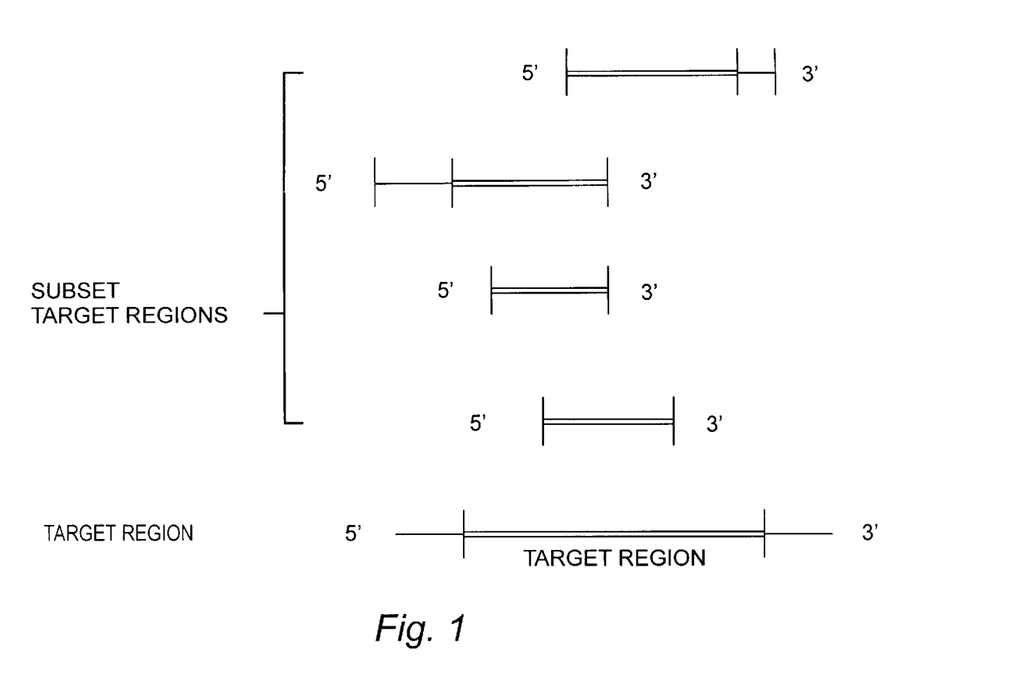
FIG. 1 illustrates several examples of subset target regions. The double line represents nucleic acid in the target region. The single line represents nucleic acid outside the target region (part of the subtargeted oligonucleotide target region).

Subtargeted oligonucleotides are targeted to a subset of the targeted oligonucleotide target region. FIG. 1 illustrates a target region and gives some examples of subset target regions. The double line in FIG. 1 represents a target region or a subset target region. The subset target region is that part of the subtargeted oligonucleotide target region which is also present in the target region of the targeted oligonucleotide. The subtargeted oligonucleotide may also have nucleotides which are not present in the targeted oligonucleotide target region. The solid line in FIG. 1 represents additional nucleotides which can make up a target site for a subtargeted oligonucleotide.

By "comprises a truncated version" is meant that the subtargeted oligonucleotide is complementary to only a subset target region and may contain additional nucleotides not complementary to the target region.

Figure 2:
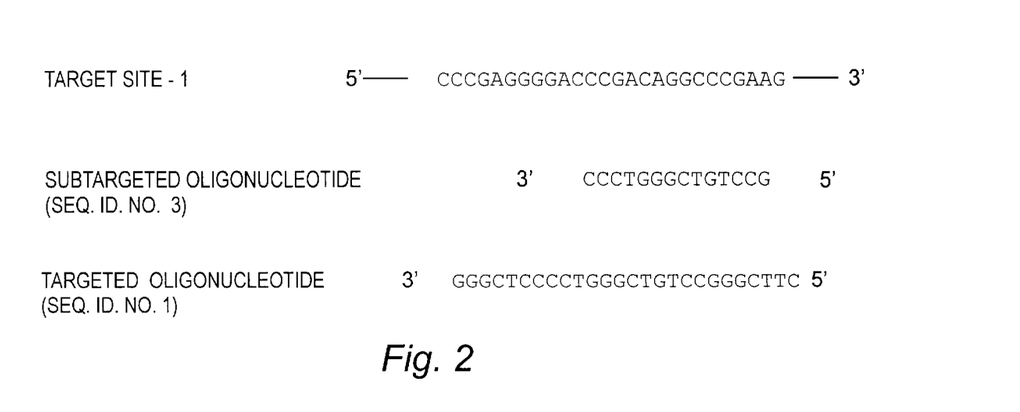
FIG. 2 illustrates target site 1, a subtargeted oligonucleotide and a targeted oligonucleotide.

FIG. 2 provides an example of a target region, a subtargeted oligonucleotide, and a targeted oligonucleotide. The subtargeted oligonucleotide contains part of the nucleic acid sequence of the targeted oligonucleotide. The region of complementarity between the subtargeted oligonucleotide and the target region is the subset target region.

Without being bound to any theory, subtargeted oligonucleotides are thought to enhance inhibition of protein synthesis and/or viral multiplication primarily by hybridizing to nucleic acid sequences or binding to protein regions, inaccessible to the corresponding targeted oligonucleotide. For example, the formation of a subtargeted oligonucleotide:target duplex may increase the chance of forming a targeted oligonucleotide: target duplex, and/or inhibit a different form of target nucleic acid than the targeted oligonucleotide. Different forms of RNA may arise due to nucleic acid processing (e. g., splicing of mRNA), and changes in the intracellular environment. Changes in the intracellular environment include different microenvironments within the cell such as in the cytoplasm versus the nucleus, and the association of proteins with nucleic acid at different stages of RNA processing.

Preferably, the subtargeted oligonucleotide, as illustrated in FIG. 2, contains only nucleotides present in the targeted oligonucleotide and is targeted to a subset target region 40 to 60 percent the size of the target region. Presumably, as the subtargeted oligonucleotide becomes larger, it is less likely to hybridize to regions inaccessible to targeted oligonucleotides.

The subtargeted oligonucleotide should be 7 nucleotides or more in length. The smaller the subtargeted oligonucleotide, the more likely the subtargeted oligonucleotide will hybridize to non-target sequences. Hybridization to non-target sequences may lead to unwanted toxicity and thus should be avoided.

The sugar groups of the nucleotide subunits of the oligonucleotides described herein may be ribose, deoxyribose, or modified derivatives thereof such as O-methyl methyl ribose. The nucleotide subunits may by joined by linkages such as phosphodiester linkages, modified linkages, or by non-nucleotide moieties that do not prevent hybridization of the oligonucleotide. Modified linkages include those linkages in which a standard phosphodiester linkage is replaced with a different linkage, such as a phosphorothioate linkage, a methylphosphonate linkage, a phosphodithioate linkage, or a phosphoselenate linkage.

The oligonucleotide combinations described herein can be made up of two oligonucleotides each having a different predominant linkage. "Predominant linkage" refers to the type of linkage present in the highest percentage, of the total linkages, in an oligonucleotide. Preferably, the oligonucleotide contains linkages resistant to exonuclease degradation such as methylphosphonate or phosphorothioate linkages. More preferably, the predominant linkage of the oligonucleotide is resistant to exonuclease degradation.

In another aspect, a method and compositions for inhibiting protein production is provided using two purified targeted oligonucleotides. The two purified oligonucleotides are targeted to different nucleic acid sequences coding for the same protein. Preferably, the two oligonucleotides are targeted to nucleic acid sequences more than 3 nucleotides apart.

In another aspect, a method and compositions for inhibiting the multiplication of a foreign organism is provided.

The described methods include the use of the featured compositions described above; 1) two purified targeted oligonucleotides, 2) a purified targeted oligonucleotide and a purified subtargeted oligonucleotide, and 3) a purified targeted oligonucleotide and a non-targeted phosphorothioate oligonucleotide. The two purified oligonucleotides are targeted to different nucleic acid sequences. Preferably, these different nucleic acid sequences are more than 3 nucleotides apart.

Foreign organisms are those organisms, such as bacteria, fungi, parasites, and viruses, which may infect higher level organisms such as humans, animals, and plants. Parasites include organisms living in or on another organism such as a plant, animal, or human. Animal and human parasites of medical importance include intestinal protozoa such as amoebas, flagellates, coccidia, and microsporidia; blood protozoa such as malaria; and helminths such as nematodes, cestodes, and trematodes.

In another aspect, a method and compositions for treating cell proliferative diseases is described. Cell proliferative diseases include inappropriate pathological cell growth such as exists in cancer cells, malignant cell proliferation and benign proliferative diseases. The use of oligonucleotides to treat cell proliferative diseases is described by Fung et al., supra, hereby incorporated by reference herein. The methods and compositions described herein enhance the ability of oligonucleotides to inhibit synthesis of a regulatory element responsible for cell proliferative disease. By "regulatory element" is meant a component of the cell encoded for by nucleic acid that controls cell growth and/or cell division.

In another aspect, a therapeutic composition comprising a purified targeted oligonucleotide consisting essentially of from 9 to 100 nucleotides able to hybridize with the HIV nucleic acid SEQ. ID. NO. 5: CCCGAGGGGA CCCGACAGGC CCGAAG and a purified subtargeted oligonucleotide is provided. The subtargeted oligonucleotide includes a truncated version of the targeted oligonucleotide. The therapeutic composition is able to reduce the normal activity of HIV nucleic acid needed for viral multiplication.

By "hybridize" is meant that the oligonucleotide can form a duplex with its target nucleic acid to reduce the normal activity of the target nucleic acid. Hybridization between anti-viral oligonucleotide and target HIV nucleic acid is preferably specific to target viral nucleic acid under in vivo conditions. However, anti-viral oligonucleotides that can form a duplex with both the viral target site and non-target cellular sites under in vivo conditions may still be useful as anti-viral agents in vivo. In vivo effectiveness may arise due to different factors such as adequate discrimination between inhibition of viral nucleic acid activity and cellular nucleic acid activity.

By "consisting essentially of" is meant to include oligonucleotides having sufficient contiguous nucleotides complementary to the target sequence to hybridize under physiological conditions and any additional nucleotides associated therewith which do not prevent (and preferably do not enhance) such hybridization. Preferably, consisting essentially of a nucleic acid sequence means the oligonucleotide contains a nucleic acid sequence which has 0 to 5% nucleotide base difference (excluding RNA or DNA derivatives), from a specified sequence, has the claimed activity (e. g., anti-HIV activity), and may contain up to 4 additional nucleotides. The additional nucleotides may be complementary or non-complementary to HIV nucleic acid.

"RNA and DNA derivatives" refer to RNA and DNA molecules having the same complementary base pair hybridization properties. RNA and DNA derivatives have different sugar groups (i.e., ribose versus deoxyribose), and may differ by the presence of uracil in RNA and thymine in DNA.

The targeted oligonucleotide preferably has the nucleic acid sequence given by SEQ. ID. NO. 1 or the RNA derivative thereof SEQ. ID. NO. 2. The subtargeted oligonucleotide is preferably 40–60% the size of SEQ. ID. NO. 1. More preferably, the subtargeted oligonucleotide is given by SEQ. ID. NO. 3 or the RNA derivative thereof SEQ. ID. NO. 4. The invention also features methods for use of the above oligonucleotides and vectors encoding such oligonucleotides.

A specific application of these methods and compositions is described for the inhibition of HIV nucleic acid activity. The use of a subtargeted oligonucleotide synergistically increased the effect of an antisense oligonucleotide, thereby increasing the efficacy of the antisense oligonucleotide to inhibit HIV multiplication. Advantages of increased efficacy include reducing the effective concentration of antisense oligonucleotide needed for clinical treatment.

Other features and advantages of the invention will be apparent from the following description of the preferred embodiments thereof, and from the claims.

DESCRIPTION OF THE PREFERRED EMBODIMENTS

The present invention describes methods and compositions for synergistically inhibiting protein production and/or the multiplication of a foreign organism. The featured oligonucleotide compositions include the combination of a first targeted oligonucleotide and either 1) a subtargeted oligonucleotide, 2) a second targeted oligonucleotide, or 3) a non-targeted phosphorothioate oligonucleotide.

The featured oligonucleotide compositions may also be used in conjunction with additional targeted and/or subtargeted oligonucleotide(s). Additional targeted oligonucleotide(s) are targeted to a different nucleic acid sequence than the other targeted oligonucleotide(s) present in the initial composition. Similarly, additional subtargeted oligonucleotide(s) are targeted to a different subtarget region than the other subtarget oligonucleotide(s) present in the initial composition. For example, a second targeted or subtargeted oligonucleotide may be used in conjunction with a targeted oligonucleotide/subtargeted oligonucleotide composition. Similarly, a third targeted oligonucleotide can be used in conjunction with a composition containing two targeted oligonucleotides.

Synergistic inhibition refers to more inhibition than the sum of the inhibitions seen with each oligonucleotide alone, when present at the same concentrations as in combination. The present invention describes how to make and use oligonucleotide compositions to synergistically inhibit protein synthesis and/or viral multiplication.

Preferably, the synergistic inhibition is at least 10 fold greater than the sum of the individual oligonucleotide inhibitions. More preferably the synergistic inhibition is at least 100 fold. Most preferably the synergistic inhibition is at least 1000 fold.

Numerous uses of targeted oligonucleotides are known, including applications as a human therapeutic, and selection of desirable plant traits. The compositions and methods described herein can be used to enhance the effect of the targeted oligonucleotide in these, and other types, of applications wherein a targeted oligonucleotide is used to inhibit protein production and/or viral multiplication.

An example of using the methods and compositions described herein to inhibit HIV replication is provided below. The example is not limiting in the invention. Those skilled in the art will recognize that equivalent oligonucleotide compositions targeted to different regions in different organisms can be readily designed and synthesized, using this application as a guide.

Proposed Mechanisms

There are numerous mechanisms which can account for the observed synergistic effect. These mechanism include the following:

1. Synergy between the action of longer oligonucleotides working as non-sequence-specific inhibitors (non-targeted phosphorothioate oligonucleotides) and targeted oligonucleotides. Longer length non-targeted phosphorothioate oligonucleotides, for example phosphorothioate $C_{28}$, as described by Matsukura et al., supra, can inhibit HIV reverse transcriptase in a non-sequence-specific manner. Preferably, the non-target phosphorothioate is 15 nucleotides or longer in length. A mixture of a longer non-targeted phosphorothioate oligonucleotide and a targeted oligonucleotide may show synergy by a combination of non-sequence-specific inhibition of the HIV reverse transcriptase and sequence-specific (antisense) inhibition of the targeted gene (for example rev or tat). In this instance, the two oligonucleotides would act at different steps in the viral life cycle and on different components of the viral replication/expression machinery.

2. The combination of two oligonucleotides may act in concert to promote uptake of the therapeutic oligonucleotides into the cells. Increased uptake may result from the two types of oligonucleotides combining to form an aggregate, network, or other complex, that is more readily taken up into cells than one type of oligonucleotide alone. These complexes may be non-specific in nature or result from base pairing and stacking of partially complementary regions. Such complexes might bind more readily to receptors. For example, large phosphorothioate oligonucleotides can bind to CD4 receptors and inhibit binding of HIV to the receptor. If binding is mediated through cooperative charge-charge interactions, larger oligonucleotides (and likely complexes of large and small oligonucleotides) should bind more tightly to the cell surface, promoting oligonucleotide uptake.

3. The synergistic effect may be due to one oligonucleotide enhancing the ability of the other to bind in regions of tight secondary structure. The subtargeted oligonucleotide may bind to an open region, not accessible to a targeted oligonucleotide, and then open up a structured region.

For example, the subtargeted oligonucleotide may open up core viral nucleic acid. Retroviruses contain two copies of genomic RNA in each virus particle. These copies are tightly interwound or complexed in the virus core. There may be interstrand base pairing between the two strands. One of the oligonucleotides could bind to one strand and disrupt this interstrand base pairing and thus allow the other oligonucleotide to bind to its target site. This mechanism is based upon both HIV strands having the same polarity (plus strands), while both the targeted oligonucleotide and the subtargeted oligonucleotide have the same polarity (in this mechanism, minus strands) and are overlapping (one being a truncated version of the other).

4. The smaller subtargeted oligonucleotide might be able to penetrate virus particles; whereas, the larger targeted oligonucleotide may not. Thus, synergy may be due to an effect of the larger oligonucleotide within the infected cell and an effect of the smaller oligonucleotide on events occurring within the highly protected environment of the virus particle.

5. The combination of the two oligonucleotides may promote retention of the two oligonucleotides within the cells. One problem with therapeutic oligonucleotides is back-diffusion or other egress from cells of oligonucleotides. The combination of two oligonucleotides might not interact outside the cell. However, in the changed environment within the cell they might complex or aggregate in such a way as to limit efflux from the cell. Thus, the intracellular concentration of the oligonucleotides may reach and maintain higher levels for a longer period of time with consequent enhancement of their therapeutic activity.

6. The two oligonucleotides may act by binding differentially to different proteins which bind mRNA. The subtargeted oligonucleotide might bind better to a portion of the binding protein which is inaccessible to a targeted oligonucleotide, while a longer targeted oligonucleotide might bind better to a more accessible site. For example, a smaller oligonucleotide might bind into an enzyme active site where the larger targeted oligonucleotide would not fit.

On the other hand, a longer targeted oligonucleotide may bind better than a shorter subtargeted oligonucleotide to proteins where accessibility is not a problem. In this instance the increased number of bases in the longer oligonucleotide may result in increased binding to protein.

Thus, two oligonucleotides, one of which is a truncated version of the other, may synergistically function by each binding more tightly and perhaps exclusively to different proteins. The same mechanism can be applied to binding to nucleic acids where secondary and tertiary structures of the nucleic acids would cause one or the other targeted oligonucleotide molecule to bind more tightly.

7. The molecules might work at different times in the viral life cycle. Different proteins and nucleic acids are expressed, processed, exposed, or otherwise accessible or inaccessible, or important or not important, at various stages of the virus life cycle. Inhibition at more than one stage of the virus life cycle can result in synergy between a subtargeted/targeted oligonucleotide combination, or a two targeted oligonucleotide combination.

8. One oligonucleotide might have faster uptake kinetics than the other, but both might be degraded at the same rate once within the cell. The two oligonucleotides together may maintain an effective intracellular concentration for a longer period of time. The effect would be similar to dosing the patient at intervals. Similar effects should occur if the degradation kinetics or efflux kinetics of the two therapeutic oligonucleotides are different.

9. Oligonucleotides may be able to enter cells through bulk fluid uptake via pinocytosis. Two oligonucleotides could act synergistically (for example by complex formation, differential kinetics, or a non-sequence -specific effect of the larger oligonucleotide on the appropriate transport machinery) to promote efflux of the oligonucleotides from the pinocytotic vesicles into the cell cytoplasm.

10. The two oligonucleotides may bind to different regions within an mRNA molecule coding for a single polypeptide chain or to two different forms of the mRNA molecule. The target sequence may be contained within, for example, a viral genomic RNA molecule and within shorter mRNAs generated by transcription from integrated viral DNA and/or RNA processing. Different structural forms of these RNAs may exist due to intramolecular folding, packaging within virus structures (including those in the process of assembly), and/or association with proteins that bind the nucleic acid. With multiple targeted oligonucleotides, the chance increases that at least one oligonucleotide will bind to the target molecule and affect its activity This list of possible mechanisms is not intended to be an exhaustive list. Additional mechanisms are described below to further illustrate the invention.

Subtargeted Oligonucleotide Combinations

A composition made up of a targeted oligonucleotide and a subtargeted oligonucleotide may be used to inhibit production of a particular protein and/or the multiplication of a foreign organism. Subtargeted oligonucleotides are oligonucleotides targeted to a subset of the targeted oligonucleotide target region. These "subset target sites" are smaller versions of the targeted oligonucleotide target region. The subtargeted oligonucleotide may contain additional nucleotides not present in the targeted oligonucleotide which do not prevent hybridization with the subset target region. Foreign organisms are those organisms, such as viruses, bacteria, fungi, and parasites which may infect higher level organisms such as humans, other animals, and plants. When the foreign organism is a virus, inhibition of viral nucleic acid activity may include inhibiting packaging of nucleic acid, not just inhibition of protein synthesis.

As discussed above, there are several possible mechanisms through which the subtargeted oligonucleotide may be exerting its effect. Without being bound to any theory, subtargeted oligonucleotides are thought to function primarily by hybridizing to nucleic acid sequences inaccessible to the targeted oligonucleotide.

The subtargeted oligonucleotide: target duplex presumably increases the formation of a targeted oligonucleotide-:target duplex, and/or inhibits a different form of target nucleic acid than the targeted oligonucleotide.

As noted above, different forms of RNA may arise as the RNA moves from one subcellular compartment to another due changes in local microenvironments such as in the cytoplasm versus the nucleus, and the association of proteins at different stages of RNA processing. A subtargeted oligonucleotide may bind to one form of RNA, while a targeted oligonucleotide binds to a different form of RNA.

In addition, the subtargeted oligonucleotide: subset target duplex may increase the formation of a targeted oligonucleotide: target duplex by opening up the target region to the targeted oligonucleotide, or displacing proteins associated with nucleic acids. Subtargeted oligonucleotides are targeted to a subset of the target sequence. Thus, the subtargeted oligonucleotide may be able to hybridize to a nucleic acid region not accessible to the targeted oligonucleotide.

However, the targeted oligonucleotide has a longer stretch of contiguous complementary oligonucleotides to the target sequence then the subtargeted oligonucleotide. As a result, the targeted oligonucleotide may be able to displace its corresponding subtargeted oligonucleotide.

Once formed, the targeted oligonucleotide: target duplex, due to the increased complementarity to the target nucleic acid sequence, may be more stable than a subtargeted oligonucleotide: subset target duplex. A more stable oligonucleotide: target duplex is less likely to be "knocked" off due to factors such as intramolecular hydrogen bonding or nucleic acid-associated proteins.

Advantages of increased stability of oligonucleotide: RNA duplexes may include increased efficiency of hybrid arrest translation and, when the antisense oligonucleotide is DNA, increased likelihood of recognition and degradation by RNAse H. Advantages of increased stability of ribozyme:target duplexes may include keeping the substrate RNA properly aligned for enzymatic digestion.

A synergistic effect may result from the decrease in viable mRNA transcripts by one or more of the mechanisms proposed above. Viable mRNA transcripts refer to mRNA transcripts able to be translated into a complete, functional protein. Oligonucleotides that inhibit the nucleic acid activity of nucleic acid may decrease the number, or ability, of viable mRNA transcripts to code for protein. For example, antisense oligonucleotide hybridization to a pre-mRNA intron/exon junction may prevent processing of pre-mRNA into mRNA, thereby reducing the number of viable mRNA transcripts.

The target region is preferably between 16 and 100 nucleotides sequences in length, more preferably 24 to 50 nucleotides sequences in length. Preferably, the subtargeted oligonucleotide contains nucleotides present in only the targeted oligonucleotide and is targeted to a subset target region 40 to 60 percent the size of the target region. Presumably, as the subtargeted oligonucleotide becomes larger it would act more like the targeted oligonucleotide thereby reducing the synergistic effect of using the targeted/subtargeted oligonucleotide combination. For example, as the subtargeted oligonucleotide increases in size it is less likely to hybridize to a region inaccessible to a targeted oligonucleotide.

The subtargeted oligonucleotide should be 7 or more nucleotides in length. The smaller the subtargeted oligonucleotide the increased likelihood the subtargeted oligonucleotide will hybridize to non-target sequences. Hybridization to non-target sequences may lead to cell toxicity.

The target region for the targeted oligonucleotide preferably forms a secondary structure in vivo. Secondary structure has been associated with nucleic acid activity, and thus such regions may be good target sites for inhibiting nucleic acid activity. For example, structured regions of nucleic acids are often sites for recognition by enzymes and binding proteins involved in regulation of gene expression. Regions containing a secondary structure are expected to be less accessible to targeted oligonucleotides. Since subtargeted oligonucleotides may work by hybridizing to targeted regions not accessible to a targeted oligonucleotide, a subtargeted oligonucleotide may have a greater effect on a region involved in a secondary structure than a region not involved in a strong secondary structure. Regions expected to have a secondary structure can be identified using techniques known in the art. (e.g., Zuker, M, in: *Methods In Enzymology*, vol 190, p. 262 (1979)).

Two Targeted Oligonucleotides

A composition comprising two targeted oligonucleotides may be used to inhibit production of a particular protein and/or the multiplication of a foreign organism. The two oligonucleotides are preferably targeted to nucleic acid sequences more than 3 nucleotides apart which may code for the same protein or different proteins. An example of a two targeted oligonucleotide combination which appears to act synergistically, at some oligonucleotide concentrations, is the phosphorothioated oligonucleotide of sequence SEQ. ID. NO:1 and the phosphorothioated oligonucleotide of sequence SEQ. ID. NO:6 (targeted to pol ).

A targeted oligonucleotide can hybridize to a target nucleic acid sequence region and inhibit production of protein encoded for by the target nucleic acid. While nucleic acids that are not perfectly complementary may hybridize to each other under physiological conditions, the longest stretch of perfect complementarity base sequence generally determines hybrid stability. Oligonucleotides designed to hybridize to a particular sequence should have an appropriate melting temperature ($T_m$) (the temperature at which 50% of the oligonucleotide is hybridized to its target nucleic acid). The appropriate $T_m$ can be obtained by varying the probe length and nucleotide composition (percentage of G+C versus A+T). The probe length and nucleotide composition should result in a $T_m$ about 2°–10° C. higher than physiological temperature (37° C.).

The longer the complementary region on an oligonucleotide, the more hydrogen bonding to a target sequence, and in general, the higher the $T_m$. Increasing the percentage of G and C also increases the $T_m$ because G-C base pairs exhibit additional hydrogen bonding and therefore greater thermal stability than A-T base pairs. $T_m$ can be determined using techniques known in the art such as measuring hybridization by the hybridization protection assay (HPA) according to Arnold et al., entitled "Homogeneous Protection Assay," EPO application number 88308767.8, publication number 309230, and Nelson et al., in *Nonisotopic DNA Probe Techniques,* p. 275 Academic Press, San Diego (Kricka, ed., 1992) (these references are hereby incorporated by reference herein). oligonucleotides can be labeled with acridinium ester derivatives as described by Arnold, et al., PCT/US88/03361, entitled "Acridinium Ester Labeling and Purification of Nucleotide Probes," hereby incorporated by reference herein.

$T_m$ can be measured using HPA in the following manner. oligonucleotides are labeled with an acridinium ester. Oligonucleotide: target hybrids are formed in a lithium succinate buffer (0.1M lithium succinate buffer (pH 5.0), 2 mM EDTA, 2 mM EGTA, 10% (w/v) lithium lauryl sulfate) using an excess amount of nucleic acid target. Aliquots of the solution containing the nucleic acid hybrids are then diluted in the lithium succinate buffer solution. The aliquots are incubated for five minutes at various temperatures starting below that of the anticipated $T_m$ and increasing in 2°–5° C. increments. This solution is then diluted with a mild alkaline borate buffer (0.15M sodium tetraborate, (pH 7.6), 5% (v/v) TRITON™ X-100) and incubated at a lower temperature for ten minutes. Under these conditions the acridinium esters attached to single-stranded oligonucleotides are hydrolyzed, while acridinium esters attached to hybridized oligonucleotides are relatively protected from hydrolysis. Thus, the amount of acridinium ester molecules remaining after hydrolysis treatment is proportional to the number of hybrid molecules present in the sample. The remaining acridinium esters can be measured by monitoring the chemiluminescence produced by addition of hydrogen peroxide and alkali to the solution. Chemiluminescence can be measured in a luminometer (e.g., the Gen-Probe LEADER I® or LEADER 50®). The resulting data is plotted as percent of maximum signal (usually from the lowest temperature) versus temperature. In this assay, the $T_m$ is determined to be the temperature at which 50% of the maximum signal remains. In addition to the method above, $T_m$ may be determined by isotopic methods well known to those skilled in the art (see e.g., Hogan et al., supra).

The optimal oligonucleotide size of a targeted oligonucleotide should take into account different factors including different mechanisms of action and cellular uptake. Targeted oligonucleotides are preferably 18 to 100 nucleotides, more preferably, 18 to 50 nucleotides in length, and most preferably, 20–35 nucleotides in length.

Oligonucleotides containing longer nucleic acid sequences of complementarity to a target sequence offer several advantages compared to shorter oligonucleotides, including increased target specificity and increased stability of the oligonucleotide: target duplex. The increased stability of the oligonucleotide: target duplex may facilitate the oligonucleotide nucleic acid inhibitory effect in different manners. For example, if the primary effect is translation arrest, the increased stability of the duplex could increase translation arrest by preventing a ribosome from displacing the oligonucleotide.

Another example of a possible mechanism involves degradation of the RNA strand of a DNA: RNA HIV duplex with an enzyme having RNase H activity. In this instance, the increased stability of the duplex increases the likelihood that the duplex is acted on by the enzyme. To be degraded by RNase H activity, the anti-HIV oligonucleotide in the DNA: RNA HIV duplex preferably contains three or more contiguous phosphodiester or phosphorothioate linkages.

Possible disadvantages of oligonucleotides having a longer length include a decrease in oligonucleotide uptake and a possible increase in host toxic effect. The degree of these effects are, at least in part, determined by the size of the oligonucleotide and types of oligonucleotide linkages. Possible host toxic effects may be more pronounced, for example, using oligonucleotides containing phosphorothioate linkages.

Without being bound to any theory, the use of two targeted oligonucleotides is expected to exert their effect by inhibiting a particular RNA nucleic acid more than either targeted oligonucleotide alone. Further inhibition may arise due to hybridization to different forms of RNA or to more efficient inhibition of a particular form of RNA.

Non-Targeted and Targeted Oligonucleotide Combination

A non-targeted and targeted oligonucleotide combination is preferably used to inhibit a retrovirus. Non-targeted oligonucleotides are longer length oligonucleotides joined by phosphorothioate linkages. Preferably, the non-targeted oligonucleotide is 20 to 100 nucleotides in length, more preferably 25 to 50 nucleotides in length.

Without being bound to any theory, non-targeted oligonucleotides are thought to function in a non-sequence specific manner primarily by inhibiting reverse transcriptase. However, as noted above, longer chain phosphorothioate oligonucleotide may also increase uptake of a targeted oligonucleotide into a cell. Thus, while non-targeted phosphorothioate oligonucleotide are particular useful for inhibiting retroviruses such as HIV, there is no intention to limit the use of non-targeted phosphorothioate oligonucleotides to inhibit a retrovirus.

Sense and aptamer oligonucleotides

Sense oligonucleotides are oligonucleotides having the same nucleic acid sequence as a nucleic acid sequence present on a targeted nucleic acid. Sense oligonucleotides are directed to a particular protein target. Aptamers (Ellington and Szostak, *Nature* 346:812 (1990) are oligonucleotides selected for their ability to bind to specific protein target. Aptamers directed to a specific target can bind to the specific target. Aptamers may be made up of RNA and/or DNA and may be single or double-stranded.

Without being bound to any particular theory, sense oligonucleotides are thought to inhibit nucleic acid activity by inhibiting proteins involved in nucleic acid activity. Proteins involved in nucleic acid activity include proteins such as ribosomal binding proteins and tRNA synthetase which help bring about the production of a protein from nucleic acid (e.g., proteins involved in transcription and/or translation).

Similarly, aptamers are thought to function by binding specifically to the active site of enzymes or other macromolecules and inhibiting the normal biological activity of their targets.

Combinations of sense or aptamer oligonucleotides and targeted oligonucleotides may display synergy when targeted to, and directed to, the same or different nucleic acid or protein target. For example, the combination of a targeted oligonucleotide targeted to a nucleic acid, and a sense oligonucleotide directed to a protein involved in nucleic acid activity, may inhibit the targeted nucleic acid more than the sum of the inhibition of the targeted and sense oligonucleotide acting alone.

A targeted/sense or aptamer oligonucleotide combination can also be used to inhibit production of more than one protein involved in a biosynthetic or regulatory pathway. Such a combination should be more effective in inhibiting the multiplication of a foreign organism than either compound used alone.

Thus, a targeted oligonucleotide/sense or aptamer oligonucleotide combination, like other oligonucleotide combinations described herein (e.g., a two targeted oligonucleotide combination, a targeted oligonucleotide/enhancer combination or a targeted oligonucleotide/non-targeted oligonucleotide combination) may be more effective then either oligonucleotide acting alone because either oligonucleotide acting alone may not completely block a biosynthetic or regulatory pathway, or completely inhibit a particular nucleic acid. However, inhibiting the production of several proteins of a pathway, or a single nucleic acid in multiple ways, may completely, or almost completely, block the pathway or inhibit the particular nucleic acid.

Methods for selecting sense or aptamer oligonucleotides directed against a specific protein are known in the art. Examples of these methods include those methods described by Mills et al. *Proc. Natl. Acad. Sci. USA* 58:224 (1967), Green et al. Nature 347:406 (1990), and Tuerk and Gold *Science* 249:505 (1990), which show the use of in vitro evolution techniques to select RNA molecules with desired properties. Ellington and Szostak *Nature* 346:818 (1990), and Bock et al. *Nature* 355:564 (1992) describe the selection of DNA oligonucleotides. The field has recently been reviewed by Burke and Berzal-Herranz *FASEB J* 7:106 (1993). These references are hereby incorporated by reference herein.

Therapeutic activity

One use of the present invention is to increase the therapeutic efficacy of targeted oligonucleotides. The therapeutic use of targeted oligonucleotide/subtargeted oligonucleotide, two targeted oligonucleotides, or a targeted oligonucleotide/non-targeted oligonucleotide, combination generally involves inhibiting target nucleic acid activity, more than essential cellular nucleic acid activity. Essential cellular nucleic acid activity is nucleic acid activity needed for cell growth and functioning.

Targeted oligonucleotides or subtargeted oligonucleotides which cannot adequately discriminate between target nucleic acid and non-target essential cellular nucleic acid are less preferred because of possible cell toxicity. Generally, unwanted toxicity can be reduced or eliminated by decreasing the concentration of a drug. However, the lower concentration may be therapeutically ineffective. The described oligonucleotide compositions acting synergistically inhibit a target nucleic acid at a lower oligonucleotide concentration. As a result, oligonucleotides that might be too toxic at effective doses may be used effectively at a lower non-toxic concentration. Thus, the combination of the two oligonucleotides may allow discrimination between target and non-target nucleic acid, even when the individual oligonucleotides do not adequately discriminate at their effective concentrations.

Before testing in vivo, the ability of a targeted oligonucleotide or subtargeted oligonucleotide to hybridize to a particular target site can be assessed. For example, the hybridization behavior of an antisense oligonucleotide can be measured in essentially physiological conditions. Similarly, the ability of a ribozyme to hybridize and cleave its target nucleic acid sequence can be assayed in essentially physiological conditions.

Exact duplication of in vivo conditions is extremely difficult because the intracellular environment is very complicated and not completely known. Furthermore, there are many nucleic acid binding proteins present in cells, which may affect accessibility and activity of target sequences.

In vivo hybridization activity can be modeled in vitro (e.g., using standard solutions that approximate condition found in cells or extracellular fluids). Hybridization can be determined using an in vitro quantitative assay, according to Kohne U.S. Pat. No. 4,851,330, or Maniatis et al. *Molecular Cloning,* (New York, Cold Spring Harbor Press, 1982) or an oligonucleotide screening assay.

The oligonucleotide screening assay can be used to test the ability of oligonucleotides to hybridize to a target sequence under different conditions. The assay is preferably carried out by contacting a nucleic acid target sequence with an oligonucleotide, adding RNAse H, then measuring the amount of remaining target sequences using an acridinium ester-labeled probe under stringent hybridization conditions. Nelson et al., "Detection Of Acridinium Esters By Chemiluminescence" in: *Nonisotopic DNA Probe Techniques,* (Kricka ed., Academic Press, 1992) pp. 275–311, hereby incorporated by reference herein, describe using AE labeled probes to assay for target nucleotide sequences.

The acridinium ester attached to a single-stranded oligonucleotide is susceptible to hydrolysis and rendered non-chemiluminescent under mild alkaline conditions. However, the acridinium ester present in hybridized nucleic acid (e.g., probe: mRNA) is relatively resistant to hydrolysis. Hybridization of probe: mRNA can be measured by the chemiluminescence produced from the acridinium ester upon the addition of hydrogen peroxide followed by alkali. Chemiluminescence can be measured in a luminometer (e.g., LEADER 1™, LEADER 50™, LEADER 250™ and LEADER 450™ these luminometers are available from Gen-Probe Incorporated).

An oligonucleotide screening assay can be carried out as follows:

1) Hybridize oligonucleotides to their target nucleic acids in a solution, such as an aqueous physiological buffer. An example of a target nucleic acid is purified HIV mRNA. Hybridization can be carried out using 0.9 pmol of target mRNA, 0.1 pmol acridinium ester-labeled probe, in 100 μL of a physiological buffer, at 37° C. for 2 hours. The reactions are divided to make duplicates at 1×final buffer concentration for optimal RNase H enzyme activity.

2) *E. coli* RNase H (Life Technologies, Gaithersburg, Md., 0.4 U/reaction) is added to one of the two duplicate reactions. The other duplicate reaction lacks RNase H and serves as the (−) RNase H control. The reactions are incubated at 37° C. for 1 hour, stopped by denaturing at 95° C. for 5 minutes, and placed directly on ice.

3) Aliquots of the reaction mixtures are hybridized with the appropriate phosphodiester acridinium ester-probe. Appropriate acridinium ester-labeled probes can hybridize to the same nucleic acid sequence as the test oligonucleotide and contain an acridinium ester in the complementary region. The acridinium ester-labeled probe is hybridized at 60° C. for 1 hour. Control hybridization reactions are performed using acridinium ester-probes expected to hybridize to a region other than the target nucleic acid sequence.

4) Aliquots are diluted in hybridization buffer (0.1M lithium succinate buffer (pH 5.0), 2 mM EDTA, 2 mM EGTA, 10% (w/v) lithium lauryl sulfate). Fifty microliter replicates are hydrolyzed in 12×75 mm luminometer tubes with 300 µL of 0.15M sodium tetraborate (pH 7.6), 5% (v/v) Triton X-100 at 60° C. until non-hybridized labeled probes are fully hydrolyzed (usually 6–8 minutes). Chemiluminescence is brought about using a single injection of 1.5N NaOH, 0.1% $H_2O_2$ and measured in a luminometer.

As would be appreciated by one skilled in the art, variations of this procedure can be performed. For example, the assay can be carried out using different amounts of reagents and incubation times.

If the compositions described herein inhibit essential cellular nucleic acid activity, they may still be able to be used as therapeutics by being targeted to certain types of cells. For example, liposomes containing recognition molecules targeted to HIV-infected cells may be used to deliver the therapeutic composition to only HIV-infected cells.

Synthesis Of Oligonucleotides oligonucleotides containing phosphodiester linkages as well as modified linkages can be synthesized by procedures known in the art. For example, Caruthers et al., in: *Methods In Enzymology*, vol. 154, p. 287 (1987), describe using standard phosphoramidite solid-phase chemistry to join nucleotides by phosphodiester linkages; Bhatt, U.S. Pat. No. 5,252,723 describes a procedure for synthesizing oligonucleotides containing phosphorothioate linkages; and Klem et al., entitled "Improved process for the synthesis of oligomers" PCT WO92/07864, describe the synthesis of oligonucleotides having different linkages including methylphosphonate linkages.

Administration of Oligonucleotides

The present invention may be used as a human therapeutic for treating different afflictions including viral infections, bacterial infections, parasitic infections, and cell proliferation diseases. The described oligonucleotides can be used to treat patients using different formulations and routes of administration. Suitable routes of administration include intramuscular, aerosol, oral (tablet, liquid suspension, or pill form), topical, systemic, ocular, intravenous, intraperitoneal and intrathecal.

Pharmacological considerations such as toxicology, pharmacokinetics, absorption, distribution, metabolism and excretion should also be taken into account. These considerations relate to the ability of the oligonucleotide to reach its target site, inhibit the propagation of a foreign organism or host nucleic acid, and possibly cause side effects adversely affecting patients. Different pharmacological considerations can be evaluated using techniques known in the art.

The described oligonucleotides may be introduced as naked oligonucleotides, through expression vectors (encoding the oligonucleotide), by use of iontophoresis, or as physiologically acceptable formulations. Suitable formulations include the use of a liposome, a controlled release vehicle, ion paired molecules, covalently attached adducts, and other pharmacologically suitable methods of delivery.

Different types of delivery strategies are useful in the present invention, including oligonucleotide modifications, particle carrier drug delivery vehicles, and retroviral expression vectors. Oligonucleotides joined by phosphodiester linkages are slowly taken up by cells. To enhance cellular uptake, the oligonucleotide may be modified at the phosphodiester linkages to reduce its charge. For example, the individual nucleotides may be joined by methylphosphonate linkages or phosphorothioate linkages.

Modification of oligonucleotides to reduce charge is just one approach to enhance the cellular uptake. Modifications can also be designed to reduce susceptibility to nuclease degradation (e.g., use of methylphosphonate or phosphorothioate linkages).

Drug delivery vehicles can be chosen for both systemic and topical administration. These vehicles can be designed to serve as a slow release reservoir or to deliver their contents directly to the target cell. An advantage of using some direct delivery drug vehicles is that multiple molecules are delivered per uptake. Such vehicles have been shown to increase the circulation half-life of drugs that would otherwise be rapidly cleared from the blood stream. Some examples of such specialized drug delivery vehicles which fall into this category are liposomes, hydrogels, cyclodextrins, biodegradable nanocapsules, and bioadhesive microspheres.

The use of liposomes as drug delivery vehicles offers several advantages. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acids remain biologically active. For example, a liposome delivery vehicle originally designed as a research tool, Lipofectin, can deliver intact nucleic acid molecules to cells.

Specific advantages of using liposomes include the following: they are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

The described oligonucleotides may be systemically administered. Systemic absorption refers to the entry of drugs into the blood stream followed by distribution throughout the entire body. Administration routes which lead to systemic absorption include: intravenous, subcutaneous, intraperitoneal, and intranasal. Each of these administration routes delivers the oligonucleotide to accessible diseased cells. Following subcutaneous administration, the therapeutic agent drains into local lymph nodes and proceeds through the lymphatic network into the circulation. The rate of entry into the circulation has been shown to be a function of molecular weight or size. The use of a liposome or other drug carrier localizes the oligonucleotide at the lymph node. The oligonucleotide can be modified to diffuse into the cell, or the liposome can directly participate in the delivery of either the unmodified or modified oligonucleotide into the cell.

A liposome formulation which can associate oligonucleotides with the surface of lymphocytes and macrophages is also useful. This will provide enhanced delivery to HIV-infected cells by taking advantage of the specificity of macrophage and lymphocyte immune recognition of infected cells.

Intraperitoneal administration also leads to entry into the circulation with the molecular weight or size of the oligonucleotide-delivery vehicle complex controlling the rate of entry.

The chosen method of delivery will result in entry into the afflicted cells, and molecules should have some nuclease resistance for optimal dosing. Most preferred delivery methods include liposomes (10–400 nm), hydrogels, controlled-release polymers, and other pharmaceutically applicable vehicles, and microinjection or electroporation (for ex vivo treatments).

The exact dosage and number of doses will depend upon the data from clinical trials. Several factors such as the delivery vehicle, disease indication, the route of administration, and the linkage joining the oligonucleotide will affect the dosage. The expected dosage is between 0.001–200 mg/kg of body weight/day. The duration of treatment will extend at least through the course of the disease symptoms.

Establishment of therapeutic levels of oligonucleotides within the cell is dependent upon the rates of uptake and efflux degradation. Decreasing the degree of degradation prolongs the intracellular half-life of the oligonucleotide. Thus, chemically-modified oligonucleotides, e.g., with modification of the phosphate backbone, may require different dosaging.

AIDS therapeutic oligonucleotides can be targeted to different HIV activities. Targeting is generally based on an HIV nucleic acid sequence. However, some targeting can also be achieved by using oligonucleotides containing phosphorothioate linkages. Phosphorothioate linkages increase oligonucleotide stability, facilitate oligonucleotide uptake, and enable the oligonucleotide to inhibit HIV propagation by a mechanism which appears to be largely sequence independent. Thus, phosphorothioate linked oligonucleotides can inhibit HIV by targeting, based on their nucleic acid sequence, a specific HIV target site, and inhibit other HIV target sites by a mechanism not dependent on a specific nucleic acid sequence.

Oligonucleotides having phosphorothioate linkages inhibit viral reverse transcriptase, and may also inhibit gp120 binding to CD4 receptor and phosphorylating activity of PKC. The viral reverse transcriptase inhibitory effect increases as the size of the phosphorothioate oligonucleotide increases, and appears to be applicable for other viral reverse transcriptases. Oligonucleotides having phosphorothioate linkages are described by Cohen et al., U.S. Pat. No. 5,264,423, and Kinchington et al., *Antiviral Research,* 17:53–62, 1992.

An example of an HIV target site is the HIV nucleic acid sequence denoted by SEQ. ID. NO. 5 ("target site 1"). Target site 1 is present in exons coding for tat, rev, env, and nef. The presence of the same target site in more than one gene is due to overlapping exons in the HIV genome. As a result of the overlapping exons several genes in the HIV genome contain many of the same nucleic acid sequences (Schwartz et al., *Journal of Virology* 64:2519 (1990)).

Target site 1 is a conserved region of the HIV genome expected to have a secondary structure. A secondary structure arises from the formation of intramolecular hydrogen bonds between complementary nucleotides. The weaker the secondary structure, the less likely the formation of intramolecular hydrogen bonds.

A conserved region is a nucleic acid region present in at least three different strains of HIV which can hybridize to a particular oligonucleotide in vivo such that the nucleic acid activity of in each strain of HIV will be inhibited. Conserved regions can be identified using standard techniques known in the art (e.g., comparing the primary nucleic acid sequence of different HIV strains then testing for hybridization to a particular oligonucleotide). Preferably, conserved regions have no more than a 10% a percent difference in nucleotide sequence between two different strains of HIV.

Target site 1 has several nucleotide regions that would be expected to be involved in formation of secondary structure. In particular, target site 1 has regions that contain three contiguous C residues and one region containing four contiguous G residues. These regions may be involved in the formation of a secondary structure.

Secondary structure is associated with target function. Accordingly, hybridization to regions of secondary structure can be a particularly effective means for inhibiting nucleic acid activity. However, a problem with targeting secondary acid activity is forming an oligonucleotide:target duplex. The intramolecular hydrogen bonding creating the secondary structure is expected to inhibit the formation of an oligonucleotide:target duplex.

Anti-HIV oligonucleotides can effectively function as therapeutic agents by inhibiting viral propagation without gravely affecting the patient. In use as a therapeutic, it is possible there will be some adverse side effects. An overall therapeutic effect can be obtained by providing an overall benefit to the patient, such as increased life expectancy and increased responsiveness of the immune system. Adverse effects can be reduced using standard medical techniques and include considerations such as dosage regime. For example, anti-HIV oligonucleotides having a low therapeutic index can be used at lower concentrations over a continuous time period. Anti-HIV oligonucleotides which cannot adequately discriminate between HIV and essential cellular nucleic acid, and inhibits HIV nucleic acid to the same extent that it inhibits essential cellular functions, are less preferred. Such oligonucleotides may be able to act as a therapeutic by being delivered to only HIV infected cells (e.g., using liposomes containing recognition molecules targeted to HIV infected cells).

Oligonucleotide toxicity can be evaluated before therapeutic administration using models such as cellular assays and test animals. Cellular assays can be used to measure the cytotoxic effect of an agent and its ability to inhibit HIV propagation. (For example, see Weislow et al., *J Natl Cancer Inst* 81:577–586, 1989.) Preferably, test animals are used to measure the toxicity of anti-HIV oligonucleotides.

Examples are provided to illustrate different aspects and embodiments of the present invention and is not intended in any way to limit the disclosed invention.

EXAMPLE 1

Inhibition of HIV

The ability of a subtargeted oligonucleotide and an antisense oligonucleotide to synergistically inhibit HIV multiplication is shown below using HT4-6C cells infected with HIV. An antisense oligonucleotide was targeted to target site 1. The nucleic acid sequence of the antisense oligonucleotide is given by SEQ. ID. NO. 1. The subtargeted oligonucleotide, whose nucleic acid sequence is given by SEQ. ID. NO. 3 is a truncated version of SEQ. ID. NO. 1. The nucleotide groups of both the subtargeted oligonucleotide and the antisense oligonucleotide were joined by phosphorothioate groups and contained deoxyribose moieties.

HT4-6C cells were detached using trypsin-EDTA for 8–10 minutes at 37° C. The cells were then centrifuged at 100 rpm for 10 minutes. Cells were resuspended in 5–10 ml of maintenance medium (Dulbecco's Modified Eagle Medium containing 10% fetal calf serum, 500 units/mg penicillin, 500 units/mg streptomycin, and 2 mM glutamine). Cells were maintained by splitting once weekly into two 75 cm$^2$ T-flasks at a concentration of $3\times10^4$ cells/ml in a total volume of 200 ml maintenance medium.

On day 0, the cells were plated into the wells of a 24 well tissue culture plate (Falcon #3047) at a concentration of $2.4\times10^4$ cells per well. The cells were incubated overnight at 37° C. The next day the medium was aspirated, and 200 μl of HIV virus at a multiplicity of infection (MOI) of 0.03 was added to each well. The plates were then incubated for 2 hours at 37° C. After the 2 hour incubation, the cells were treated with 800 μl of drug at a concentration of 1.25× (in Dulbecco'Modified Eagle Medium), of the final concentration. Antisense oligonucleotide/subtargeted oligonucleotide combinations were used at different ratios. Table 1 shows antisense oligonucleotide: subtargeted oligonucleotide combinations at a ratio of 1:1 and 10:1.

The treated cells were incubated for 3 days at 37° C. On day 4 the plate was fixed with 1 ml/well of 100% methanol for 15 minutes. The wells were then aspirated and 0.5 ml of 0.3% crystal violet stain was added to the wells. After 5 minutes the wells were washed with water and dried. Plaques were counted using a microscope.

TABLE 1

| COMPOSITION | CONCENTRATIONS (nM) | # PLAQUES | % REDUCTION |
|---|---|---|---|
| SEQ. ID. NO. 1 | 20,000 | 4 | 98 |
| | 5,000 | 9 | 94 |
| | 1,250 | 28 | 83 |
| | 310 | 54 | 67 |
| | 78 | 120 | 26 |
| SEQ. ID. NO. 3 | 20,000 | 16 | 90 |
| | 5,000 | 24 | 85 |
| | 1250 | 63 | 61 |
| | 310 | 103 | 36 |
| | 78 | 157 | 2 |
| SEQ. ID. NOs. 1 and 3 10:1 ratio | 20 | 1 | 99 |
| | 5 | 9 | 94 |
| | 1.25 | 11 | 93 |
| | 0.31 | 20 | 88 |
| | 0.078 | 85 | 47 |
| SEQ. ID. NOs. 1 and 3 1:1 ratio | 40 | 4 | 97 |
| | 10 | 3 | 98 |
| | 2.5 | 16 | 90 |
| | 0.62 | 24 | 85 |
| | 0.16 | 91 | 43 |
| AZT | 1,000 | 5 | 97 |
| | 316 | 18 | 89 |
| | 100 | 35 | 80 |
| | 31.6 | 46 | 71 |
| | 10 | 86 | 47 |

The listed concentrations refer to the combined amount of oligonucleotides. The number of plaques is an average number of the plaques per well. The percent reduction is the number of the plaques observed per well containing drug divided by the number of plaques well containing no drug (161 plaques/well).

As seen in Table 1, the combination of the subtargeted oligonucleotide and the antisense oligonucleotide was about 1,000× more potent than either oligonucleotide acting alone. The antisense oligonucleotide alone appeared to inhibit HIV replication better than subtargeted oligonucleotide alone, but not as well as AZT. HIV inhibition with the antisense oligonucleotide/subtargeted oligonucleotide combination was greater than with AZT. The ability of the antisense/ subtargeted oligonucleotide combination to inhibit HIV replication appeared to be affected by the targeted oligonucleotide to subtargeted oligonucleotide ratio. A ratio of 10 to 1 was more effective than a ratio of 1 to 1.

EXAMPLE 2

In Vivo Toxicology

In vivo toxicology can be carried out in test animals by examining the ability of an oligonucleotide combination to cause gross morphological changes in organ or blood tissue. For example, a toxicology study can be carried out as follows:

1) Oligonucleotides are injected into a test mouse by the intra-tail vein. A control mouse receives a control solution lacking oligonucleotides.

2) The effect of the tested oligonucleotides on organs, tissues, and blood parameters are measured at different time points (e.g., t=0 and at 24 hours).

Blood parameters indicative of a toxic effect include changes in the number of platelets, red blood cells, white blood cells, and hemoglobin. Examples of important organs and tissues to monitor to gauge toxic effect are spleen, liver, kidney and thymus.

EXAMPLE 3

HIV Protection Assay

This example describes an anti-HIV production assay to determine the presence of HIV and screen for oligonucleotide combinations effective in protecting against HIV. The same types of assays can be used for different foreign organisms, such as viruses and bacterium, to assay for effective oligonucleotides.

An HIV protection assay can be carried using anti-HIV oligonucleotides and standard techniques measuring cell growth. Techniques measuring cell growth include the use of dyes such as 2,3-bis[2-methoxy-4-nitro-5-sulphenyl]-2-H-tetrazolium-5-carboxanilide (XTT, Sigma Chemical Co.) to measure the cells metabolic state, the use of radioactive or modified nucleotide precursors such as BUdR (bromodeoxyuradine) to measure nucleic acid replication, and the use of oligonucleotides complementary to host nucleic acids to measure production of host nucleic acids.

Assays involving host complementary oligonucleotides to measure cell growth can be carried out using an oligonucleotide containing a detectable label such as fluorescent, chemiluminescent, enzyme or radioactive label. Oligonucleotides can be designed to hybridize to host nucleic acid sequence regions such as those present in DNA, mRNA or rRNA. Examples of such nucleotide sequence regions are known in the art and can be obtained by standard techniques. The preferred source of host target nucleic acids is rRNA. A nucleic acid having a nucleotide sequence characteristic of rRNA is generally present in a cell in much greater abundance than a nucleic acid sequence present in mRNA.

HIV infects cells containing a CD4 antigen (CD4$^+$). The major target sites are T-helper lymphocytes and cells of the monocyte/macrophage lineage. The HIV-protection assay can be preformed on such cells from persons suspected of being infected with HIV. The assay can be preformed directly on such cells, or can be preformed using lysates obtained from CD4$^+$cells. The lysate can be used to infect cells more susceptible to HIV cytopathic effects than the isolated cells.

An HIV protection assay can be carried out as follows:
1) Isolate CD4+cells from a person. Preferred cells are T-lymphocytes.
2) Incubate cells under conditions compatible with cell growth in the presence (treated cells) and absence (control cells) of an anti-HIV oligonucleotide combination. Examples of conditions compatible with cell growth are described by S. Gartner and M. Popovic, 1990, Virus Isolation and Production, pp. 53–70 in *Techniques in HIV Research,* ed. by A. Alaldocini and B. D. Walker. Stockton Press. N.Y.
3) Measure the growth of the treated and control cells at one or more time point after exposure of cells to the oligonucleotide combination.

Normal growth of control cells indicates the absence of a viral infection such as an HIV infection. Normal growth can be determined by comparing the growth of the control cells to the same type of cells which are known to be healthy.

Less than normal growth of control cells indicates the presence of some cellular disorder, such as HIV. The ability of an anti-HIV oligonucleotide to protect against HIV cytotoxicity in treated cells indicates the disorder is due to HIV and that the tested anti-HIV oligonucleotide combination can be used to treat the patient.

Due to the variability in nucleic acid sequences of different strains of HIV, the inability of an anti-HIV oligonucleotide combination to inhibit HIV cell toxicity in this assay may at times fail to indicate correctly the presence of HIV. Thus, an HIV protection assay should be used along with other assays known in the art to detect the presence of HIV. The assay is preferably used to make an initial determination regarding the suitability of a specific oligonucleotide to treat a patient infected with HIV. Patients determined to be infected with HIV by other assays, but not by the HIV protection assay, should be retested using the HIV protection assay in conjunction with a different oligonucleotide combination.

Other embodiments are with the following claims.

---

We claim:

1. A method of inhibiting multiplication of the human immunodeficiency virus in cells grown in vitro comprising the step of providing to said cells a targeted oligonucleotide and a subtargeted oligonucleotide, effective to inhibit HIV multiplication, wherein said targeted oligonucleotide consists of the nucleotide base sequence of SEQ ID NO 1, and said subtargeted oligonucleotide is a truncated version of said targeted oligonucleotide which is 40% to 60% the size of said targeted oligonucleotide.

2. The method of claim 1, wherein said subtargeted oligonucleotide has the nucleotide sequence of SEQ. ID. NO. 3: GCCTGTCGGG TCCC.

3. The method of claim 2, wherein said subtargeted oligonucleotide or said targeted oligonucleotide comprises at least one linkage selected from the group consisting of phosphorothioate linkage, phosphodiester linkage, and methylphosphonate linkage.

4. The method of claim 3, wherein said subtargeted oligonucleotide and said targeted oligonucleotide each comprise at least one phosphorothioate linkage.

5. The method of claim 4, wherein said subtargeted oligonucleotide and said targeted oligonucleotide are each completely phosthorothioated.

6. A method for enhancing the ability of a targeted oligonucleotide, which consists of a nucleotide base sequence of SEO ID NO 1 and is targeted to a portion of a HIV gene or mRNA transcribed from said genes, to inhibit complete translation of said gene, comprising the step of providing to said mRNA transcribed from said gene said targeted oligonucleotide and a subtargeted oligonucleotide, wherein said subtargeted oligonucleotide is 40% to 60% the size of said targeted oligonucleotide.

7. The method of claim 6, wherein said subtargeted oligonucleotide has the nucleotide sequence of SEO ID NO 3: GCCTGTCGGG TCCC.

8. The method of claim 7, wherein said subtargeted oligonucleotide and said targeted oligonucleotide comprises at least one linkage selected from the group consisting of phosphorothioate linkage, phosphodiester linkage, and methylphosphonate linkage.

9. The method of claim 8, wherein said subtargeted oligonucleotide and said targeted oligonucleotide are each completely phosphorothioated.

10. A method of inhibiting replication of a human immunodeficiency virus comprising the step of providing a cell infected with said human immunodeficiency virus which is cultured in vitro with an amount of a targeted oligonucleotide and a subtargeted oligonucleotide effective to inhibit replication of said human immunodeficiency virus,     wherein said targeted oligonucleotide is 9 to 100 nucleotide bases in length and will bind to nucleic acid of said human immunodeficiency virus in such a manner that it overlaps a region of the nucleotide base sequence SEQ ID NO: 5 by one or more bases, and said subtargeted oligonucleotide consists of a nucleotide base sequence which is a truncated version of said targeted oligonucleotide and is at least 7 bases in length,     wherein said targeted and said subtargeted oligonucleotides are each optionally chemically modified.

11. The method of claim 8, wherein said targeted oligonucleotide comprises at least 9 contiguous nucleotide bases complementary to SEQ ID NO 5, and said subtargeted nucleotide base sequence is a truncated version of said at least 9 contiguous nucleotide bases complementary to SEQ ID NO 5.

12. The method of claim 11, wherein said subtargeted oligonucleotide is 40% to 60% the size of said at least 9 contiguous nucleotide bases complementary to SEQ ID NO 5.

13. The method of claim 10, wherein said subtargeted oligonucleotide and said targeted oligonucleotide are each completely phosphorothioated.

14. The method of claim 11, wherein said subtargeted oligonucleotide and said targeted oligonucleotide are each completely phosphorothioated.

15. The method of claim 12, wherein said subtargeted oligonucleotide and said targeted oligonucleotide are each completely phosphorothioated.

* * * * *

UNITED STATES PATENT AND TRADEMARK OFFICE
CERTIFICATE OF CORRECTION

PATENT NO : 5,874,281
DATED : February 23, 1999
INVENTOR(S) : Dattagupta *et al.*

It is certified that error appears in the above-identified patent and that said Letters Patent is hereby corrected as shown below:

Claim 5, Column 23, Line 51, delete "phosthorothioated" and insert --phosphorothioated--.

Claim 6, Column 23, Line 54, delete "genes" and insert --gene--.

Claim 11, Column 24, Line 1, delete "claim 8" and insert --claim 10--.

Signed and Sealed this

Seventh Day of September, 1999

Attest:

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear     ( i i ) SEQUENCE DESCRIPTION: SEQ ID NO: 1:

CTTCGGGCCT GTCGGGTCCC CTCGGG        26

( 2 ) INFORMATION FOR SEQ ID NO: 2:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear     ( i i ) SEQUENCE DESCRIPTION: SEQ ID NO:2:

CUUCGGGCCU GUCGGGUCCC CUCGGG        26

( 2 ) INFORMATION FOR SEQ ID NO: 3:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear     ( i i ) SEQUENCE DESCRIPTION: SEQ ID NO: 3:

GCCTGTCGGG TCCC        14

( 2 ) INFORMATION FOR SEQ ID NO: 4:

( i ) SEQUENCE CHARACTERISTICS:
        ( A ) LENGTH: 14
        ( B ) TYPE: nucleic acid
        ( C ) STRANDEDNESS: single ( D ) TOPOLOGY: linear ( i i ) SEQUENCE DESCRIPTION: SEQ ID NO: 4 :

GCCUGUCGGG UCCC 14

( 2 ) INFORMATION FOR SEQ ID NO: 5:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear     ( i i ) SEQUENCE DESCRIPTION: SEQ ID NO: 5 :

CCCGAGGGGA CCCGACAGGC CCGAAG 26

( 2 ) INFORMATION FOR SEQ ID NO: 6:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear     ( i i ) SEQUENCE DESCRIPTION: SEQ ID NO: 6 :

GCTGGTGATC CTTTCCATCC CTGTGG 26